United States Patent [19]
Johnston et al.

[11] Patent Number: 5,993,385
[45] Date of Patent: Nov. 30, 1999

[54] SELF-ALIGNING SIDE-LOADING SURGICAL RETRACTOR

[76] Inventors: Terry Johnston, 854 Hillcrest Dr., Redwood City, Calif. 94062; Thomas Wiedenmaier, 347 Devonshire, San Carlos, Calif. 94070; Daniel Bass, 300 San Carlos Ave., El Granada, Calif. 94018; Todd Pope, 4651 19th St., San Francisco, Calif. 94114

[21] Appl. No.: 08/912,677

[22] Filed: Aug. 18, 1997

[51] Int. Cl.⁶ .................................................. A61B 17/02
[52] U.S. Cl. .................... 600/213; 600/219; 600/226; 600/231; 600/232
[58] Field of Search ................................. 600/213, 210, 600/226, 227, 231, 232, 201, 219

[56] References Cited

U.S. PATENT DOCUMENTS

| | | |
|---|---|---|
| 569,839 | 10/1896 | Roeloffs ................................. 600/213 |
| 4,896,661 | 1/1990 | Bogert et al. ....................... 600/226 X |
| 4,934,352 | 6/1990 | Sullivan, Jr. ............................ 600/213 |
| 5,795,291 | 8/1998 | Koros et al. ........................ 600/213 X |
| 5,846,193 | 12/1998 | Wright ................................ 600/232 X |

FOREIGN PATENT DOCUMENTS

| | | |
|---|---|---|
| 618652 | 9/1935 | Germany ................................ 600/227 |
| 2052998 | 2/1981 | United Kingdom ................... 600/232 |

*Primary Examiner*—Jeffrey A. Smith
*Attorney, Agent, or Firm*—Kramer & Associates; D. Scott Juneau; Terry W. Kramer

[57] ABSTRACT

A surgical retractor with interchangeable retractor blades allows the retractor blades to be positioned in an incision before being side-loaded into the retractor body and locked in place. The surgical retractor uses a nipple connector with a conical base and a rounded head which fits into and self-aligns in a corresponding socket.

26 Claims, 3 Drawing Sheets

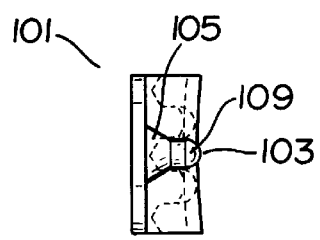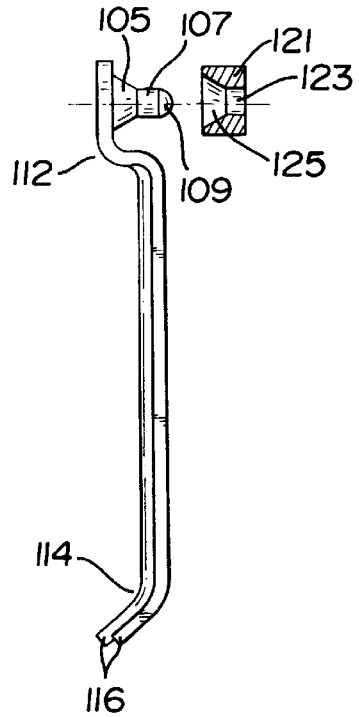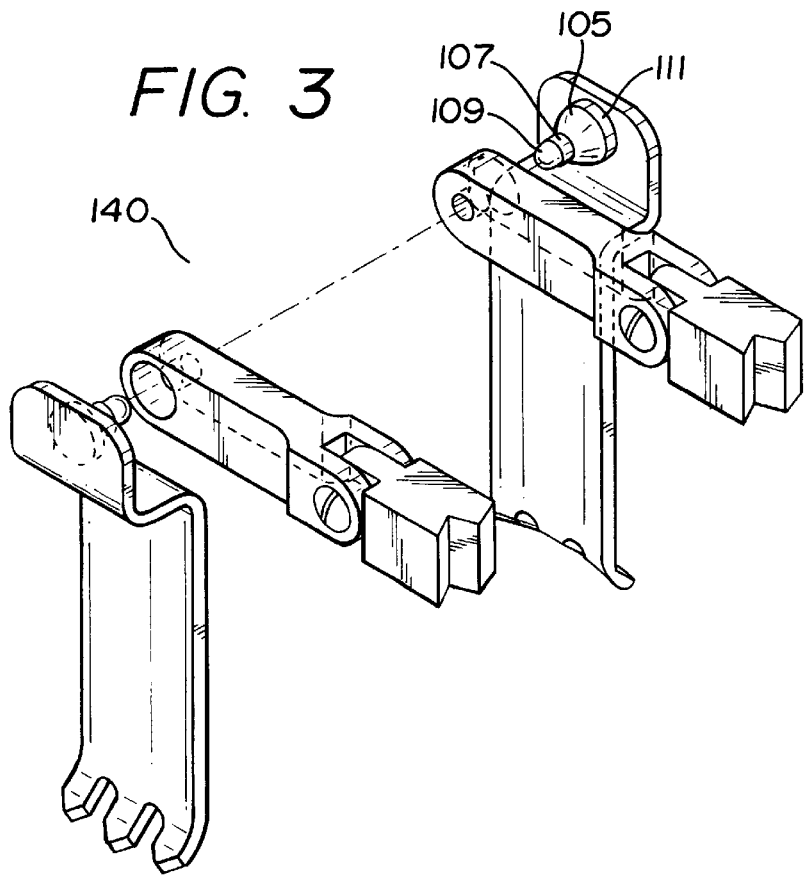

SELF-ALIGNING SIDE-LOADING SURGICAL RETRACTOR

BACKGROUND OF THE INVENTION

1. Field of the Invention

This invention relates to a surgical retractor with interchangeable retractor blades. More specifically, this invention relates to a surgical retractor with interchangeable retractor blades that are self-aligning and side-loading.

2. Description of Related Art

Surgical procedures often require the creation of a surgical exposure to allow a surgeon to reach deeper regions of the body. The surgical exposure is usually started with an incision of a suitable depth. Surgical instruments known as retractors are then inserted into the incision and used to pull back skin, muscle, and other soft tissue to permit access to the desired area.

A typical retractor is made up of a retractor body attached to one or more retractor blades. Retractor blades are smooth, thin plates with dull edges that are inserted into the incision to pull back the tissue. Retractor blades come in many different sizes depending on the particular application and physical characteristics of the patient. Retractor blades may be slightly curved or completely flat, and may have end prongs of various configurations to make it easier to pull back tissue. The retractor blades can be attached to a wide variety of retractor bodies, such as for hand-held and self-retaining retractors.

Hand-held retractors are made up of a simple grip attached to a retractor blade. The retractor blade may be fixed or interchangeable. The retractor blade is inserted into the incision, and then the grip is used to pull back the blade to create the surgical exposure. The grip may be attached at an angle to the retractor blade to make it easier to pull back on the blade. Hand-held retractors must be held in place by hand in order to maintain the surgical exposure.

Self-retaining retractors have specialized retractor bodies that allow them to maintain a surgical exposure without needing to be held in place by hand. Two common self-retaining retractors are longitudinal retractors and transverse retractors.

Longitudinal retractors have a retractor body made up of two seesawing arms with a pair of opposed retractor blades on their respective ends. The retractor body typically has a ratcheting mechanism to lock apart the two opposed retractor blades and hold them in place. This maintains the surgical exposure without the need for the retractor to be held in place by hand. The two arms may be hinged to facilitate access to the retraction site. The retractor blades may be either fixed or interchangeable.

Transverse retractors have a retractor body made up of a transverse rack with a fixed arm and a sliding arm. The fixed arm and sliding arm have opposed retractor blades on their respective ends. The sliding arm typically has a turnkey that operates a ratcheting mechanism, which ratchets the sliding arm away from the fixed arm and locks apart the retractor blades. The two arms may be hinged to facilitate access to the retraction site. The retractor blades may be either fixed or interchangeable.

For interchangeable retractor blades, there are several connector designs for allowing the retractor blades to be interchangeably attached to the retractor body. One connector is the top-loading ball snap design, which resembles the ball and snap found in common ball-and-socket wrench kits.

The ball snap design uses a top-loading socket which fits over the top of the ball snap. The retractor blades used with the ball snap design typically have a top end bent at a right angle to create a perpendicular section on which the ball snap is mounted.

The ball snap design allows the retractor blades to positively lock into the top-loading socket. This allows the entire retractor to be assembled and handed to the surgeon without the risk of the retractor blades falling off. It also permits the entire retractor to be repositioned in the incision without the risk of the retractor blades becoming detached from the retractor body.

However, many surgeons prefer to position the retractor blades first before attaching the retractor body. Positioning the retractor blades first makes it much easier for the surgeon to create a precise surgical exposure before attaching the retractor body. Pre-positioning of the retractor blades also facilitates the selection of the proper retractor blade length and width.

With the ball snap design, the surgeon must line up the sockets in the retractor body over the tops of the ball snaps before snapping the retractor blades in place. This is a difficult process, as the retractor body arms must be aligned over the ball snaps precisely in order to attach the retractor blades. This alignment process is complicated by the hinged arms and ratcheting mechanisms often found in retractor bodies.

Current side-loading designs attempt to address these problems by making it easier to load the retractor blades into the retractor body after the surgeon has pre-positioned the retractor blades. These designs use a socket or rail designed to allow the retractor blades to be loaded from the side. This allows the retractor body to be placed between the retractor blades, and then simply opened up to engage the retractor blades from the side.

However, current side-loading designs often misalign, resulting in a poor connection between the retractor blade and the retractor body. This results in the retractor blade becoming easily detached from the retractor body, even when positioned and in use in the incision.

What is needed is a surgical retractor with interchangeable retractor blades, where the retractor blades can be side-loaded into the retractor body easily and without the need for precise alignment.

SUMMARY OF THE INVENTION

One object of the invention is to provide a self-aligning, side-loading surgical retractor.

Another object of the invention is to provide a surgical retractor with interchangeable retractor blades, where the retractor blades are side-loading and self-aligning.

Accordingly, the present invention is a surgical retractor comprising a retractor blade, a nipple connector coupled to the retractor blade, the nipple connector being tapered from wide to narrow in a direction away from the retractor blade, and a retractor body having a socket, the socket configured to be able to receive the nipple connector.

BRIEF DESCRIPTION OF THE FIGURES

FIG. 1 shows a top view of one embodiment of a self-aligning side-loading retractor blade.

FIG. 2 shows a side view of another embodiment of a self-aligning side-loading retractor blade.

FIG. 3 shows a perspective view of yet another embodiment of a self-aligning side-loading retractor.

DETAILED DESCRIPTION

Figure 4:
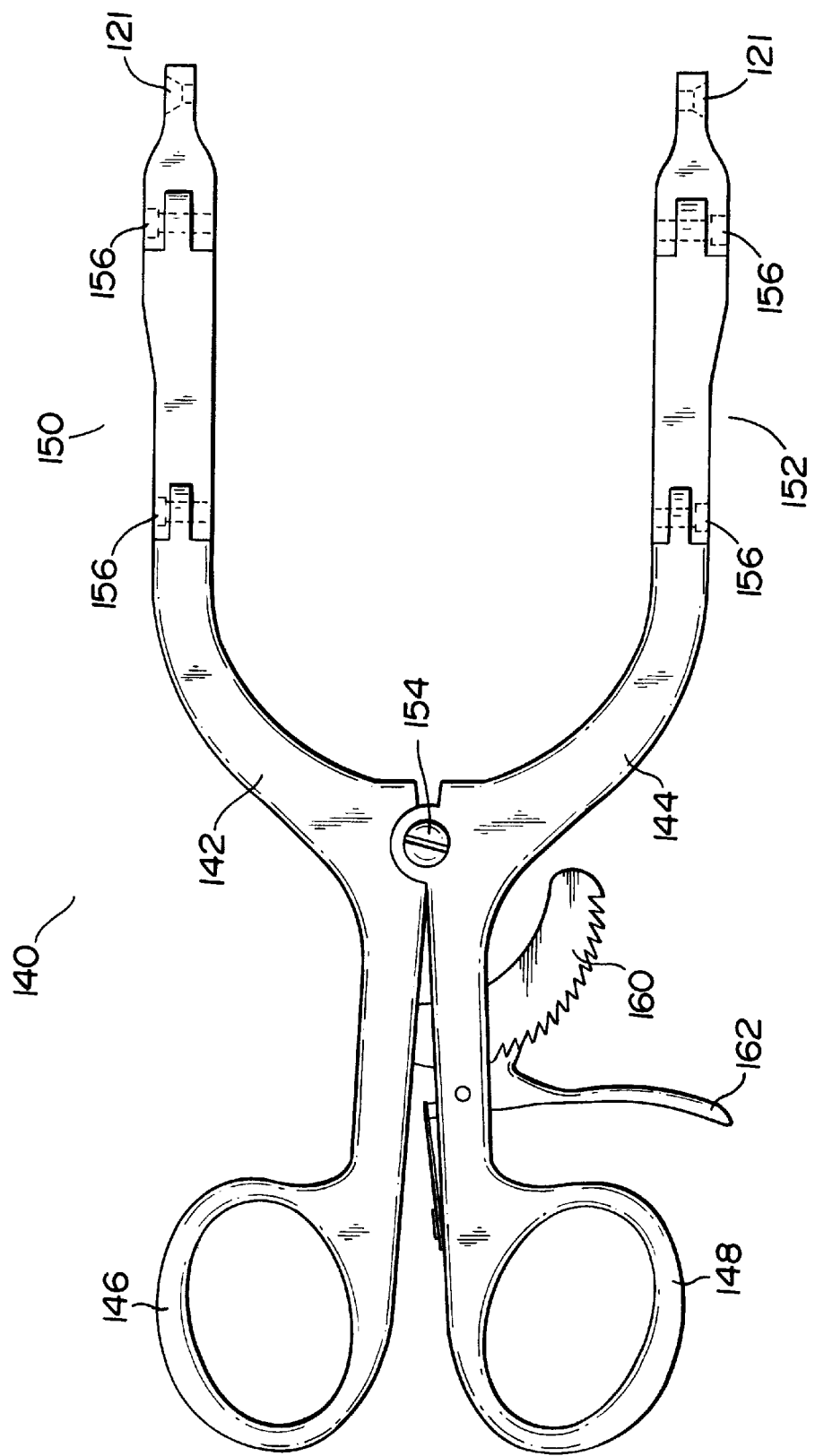
FIG. 4 is a top view of a self-aligning side-loading longitudinal retractor.

FIG. 1 is a top view of one embodiment of a self-aligning side-loading retractor blade 101. Self-aligning retractor blade 101 includes a nipple connector 103. Nipple connector 103 has a conical frustum section 105 as a base and a rounded head section 109.

Self-aligning retractor blade 101 may be rectangular or trapezoidal in shape, and may be flat or curved. Self-aligning retractor blade 101 may be contoured near its proximal end 112 to fit against a retractor arm and prevent retractor blade 101 from swinging freely. Self-aligning retractor blade 101 has a distal end 114 that may be angled to allow it to reach around and pull back soft tissue. Self-aligning retractor blade 101 may also contain one or more prongs 116 at its distal end. Prongs 116 may be of different shapes and sizes, depending on the application.

Self-aligning retractor blade 101 may be constructed of plastic, ceramic, aluminum, stainless steel, or titanium. A set of side-loading retractor blades may also be color-coded with an anodized finish, for quick selection of the desired size and length.

FIG. 2 is a side view of another embodiment of a self-aligning retractor blade 101 and a self-aligning side-loading socket 121. Nipple connector 103 has a conical frustum section 105 as a base, a generally cylindrical section 107 as a body, and a rounded head section 109.

Self-aligning socket 121 has a generally cylindrical hollow 123 and a conical frustum hollow 125. The wider region of the funnel-shaped conical frustum hollow 125 is configured to receive generally cylindrical section 107 or rounded head section 109 of nipple connector 103 and guide it towards generally cylindrical hollow 123. In this way, precise alignment of nipple connector 103 with self-aligning socket 121 is not necessary, as self-aligning socket 121 facilitates the full and proper seating of nipple connector 103 into self-aligning socket 121.

Nipple connector 103 has generally cylindrical section 107 of sufficient length such that when it is fully seated in the self-aligning socket 121, self-aligning retractor blade 101 is substantially prevented from jiggling or being pulled out by the force of the retracted tissue. Nipple connector 103 may have a slight press fit in self-aligning socket 121 to provide an even more secure connection between the two.

FIG. 3 is a perspective view of yet another embodiment of a self-aligning side-loading retractor apparatus 140. Nipple connector 103 has a first generally cylindrical section 111 and a conical frustum section 105 as a base, a generally cylindrical section 107 as a body, and a rounded head section 109.

FIG. 4 is a top view of a self-aligning side-loading longitudinal retractor 140. Longitudinal retractor 140 includes two longitudinal retractor arms 142 and 144. Longitudinal retractor arms 142 and 144 have proximal ends 146 and 148 which may contain control ends for receiving a user's fingers. Longitudinal retractor arms 142 and 144 have distal ends 150 and 152, respectively, each of which contains a self-aligning socket 121.

Longitudinal retractor arms 142 and 144 are configured to rock on a pivot 154. Retractor arms 142 and 144 may each contain one or more hinges 156. Hinges 156 permit self-aligning sockets 121 to be positioned closer to a wound or incision. Longitudinal retractor arms 142 and 144 may each contain suture holes. Suture holes permit longitudinal retractor arms 142 and 144 to be sutured in place and help prevent movement of longitudinal retractor 140 after longitudinal retractor 140 has been positioned in a desired location.

Longitudinal retractor 140 may also include a ratcheting mechanism 160 for locking retractor arms 142 and 144 apart in a desired position. Ratcheting mechanism 160 may include a release lever 162, which permits retractor arms 142 and 144 to be unlocked and brought back together again.

Figure 5:
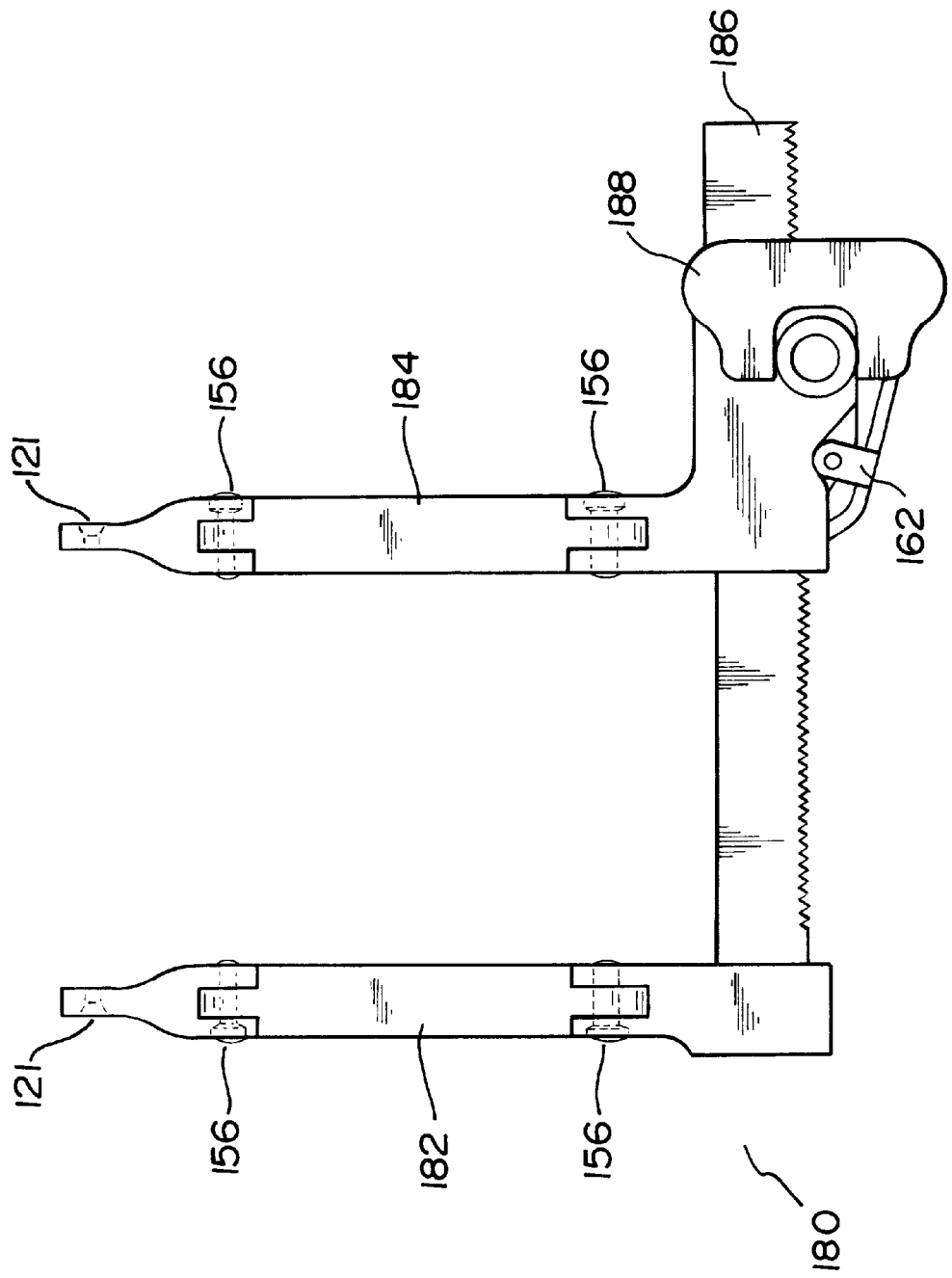
FIG. 5 is a top view of a self-aligning side-loading transverse retractor.

FIG. 5 is a top view of a self-aligning side-loading transverse retractor 180. Transverse retractor 180 includes a fixed retractor arm 182 and sliding retractor arm 184. Fixed retractor arm 182 and sliding retractor arm 184 each have a self-aligning socket 121. Fixed retractor arm 182 and sliding retractor arm 184 may each contain one or more hinges 156 and suture holes.

Fixed retractor arm 182 is fixedly mounted to a transverse rack 186. Sliding retractor arm 184 is slidably mounted to transverse rack 186. Sliding retractor arm 184 contains a ratcheting turnkey 188 which allows it to ratchet on transverse rack 186 away from fixed retractor arm 182. Sliding retractor arm 184 may be released by a release lever 162.

Self-aligning side-loading longitudinal retractor 140 and self-aligning side-loading transverse retractor 180 may be constructed of plastic, ceramic, aluminum, stainless steel, or titanium.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A surgical retractor, comprising:
    a retractor blade having a retracting surface and a nipple connector, the nipple connector being tapered from wide to narrow in a generally perpendicular direction away from the retracting surface of the retractor blade; and
    a retractor body having a socket, the socket removably receiving the nipple connector.

2. The surgical retractor of claim 1, wherein the nipple connector has a generally circular cross-section.

3. The surgical retractor of claim 1, wherein the nipple connector is not tapered continuously.

4. The surgical retractor of claim 1, wherein the retractor blade is contoured to fit the retractor body so as to prevent the retractor blade from swinging.

5. The surgical retractor of claim 4, wherein the retractor blade is bent at two right angles so as to fit around the retractor body.

6. The surgical retractor of claim 1, wherein the retractor body is a transverse retractor.

7. The surgical retractor of claim 1, wherein the retractor body is a longitudinal retractor.

8. A surgical retractor, comprising:
    a retractor blade having a retracting surface and a nipple connector, the nipple connector having a generally cylindrical section and a conical frustum section having a top and a base, the top being coupled to the generally cylindrical section, the base being coupled substantially perpendicular to the retracting surface; and
    a retractor body having a socket, the socket removably receiving the nipple connector.

9. The surgical retractor of claim 8, wherein the retractor blade is contoured to fit the retractor body so as to prevent the retractor blade from swinging.

10. The surgical retractor of claim 9, wherein the retractor blade is bent at two right angles so as to fit around the retractor body.

11. The surgical retractor of claim 8, wherein the retractor body is a transverse retractor.

12. The surgical retractor of claim 8, wherein the retractor body is a longitudinal retractor.

13. The surgical retractor of claim 8, wherein the socket has a generally cylindrical hollow and a conical frustum hollow having a mouth and a waist, the mouth being configured to receive the nipple connector and guide the cylindrical section into the waist, the waist being continuous with the generally cylindrical hollow.

14. The surgical retractor of claim 13, wherein the retractor blade is contoured to fit the retractor body so as to prevent the retractor blade from swinging.

15. The surgical retractor of claim 14, wherein the retractor blade is bent at two right angles so as to fit around the retractor body.

16. The surgical retractor of claim 13, wherein the retractor body is a transverse retractor.

17. The surgical retractor of claim 13, wherein the retractor body is a longitudinal retractor.

18. The surgical retractor of claim 8, wherein the nipple connector further includes a rounded head section coupled to the generally cylindrical section.

19. The surgical retractor of claim 18, wherein the socket has a generally cylindrical hollow and a conical frustum hollow having a mouth and a waist, the mouth being configured to receive the nipple connector and guide the rounded head section into the waist, the waist being continuous with the generally cylindrical hollow.

20. The surgical retractor of claim 19, wherein the retractor blade is contoured to fit the retractor body so as to prevent the retractor blade from swinging.

21. The surgical retractor of claim 20, wherein the retractor blade is bent at two right angles so as to fit around the retractor body.

22. The surgical retractor of claim 19, wherein the retractor body is a transverse retractor.

23. The surgical retractor of claim 19, wherein the retractor body is a longitudinal retractor.

24. A surgical retractor blade, comprising:
 a generally planar retracting section;
 a generally cylindrical section; and
 a conical frustum section having a top and a base, the top being coupled to the cylindrical section, the base being coupled to the retracting section.

25. The surgical retractor blade of claim 24, further comprising:
 a rounded head section coupled to the generally cylindrical section.

26. A surgical retractor, comprising:
 a retractor body having a socket, the socket having a generally cylindrical hollow and a conical frustum hollow, the conical frustum hollow having a mouth and a waist, the mouth configured to receive a nipple connector of a retractor blade, the waist being continuous with the generally cylindrical hollow.

\* \* \* \* \*